US00PP20050P2

(12) United States Plant Patent
Konst

(10) Patent No.: US PP20,050 P2
(45) Date of Patent: Jun. 2, 2009

(54) ***ALSTROEMERIA* PLANT NAMED 'KONPRIDE'**

(50) Latin Name: *Alstroemeria hybrida*
Varietal Denomination: Konpride

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 0 days.

(21) Appl. No.: 12/154,245

(22) Filed: May 21, 2008

(51) Int. Cl.
*A01H 5/00* (2006.01)

(52) U.S. Cl. ..... Plt./309

(58) Field of Classification Search ..... Plt./309
See application file for complete search history.

*Primary Examiner*—Annette H Para
(74) *Attorney, Agent, or Firm*—C. A. Whealy

(57) ABSTRACT

A new and distinct cultivar of *Alstroemeria* plant named 'Konpride', characterized by its compact and mounding plant habit; sturdy and strong plants; vigorous growth habit; bright pink-colored flowers; and good garden performance.

2 Drawing Sheets

Botanical designation: *Alstroemeria hybrida.*
Cultivar denomination: 'Konpride'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Konpride'.

The new *Alstroemeria* is a product of a planned breeding program conducted by the Inventor in Nieuwveen, The Netherlands. The objective of the breeding program is to create new compact potted garden *Alstroemeria* cultivars that flower early and freely and have attractive foliage and flower coloration.

The new *Alstroemeria* originated from a cross-pollination made by the Inventor in Nieuwveen, The Netherlands on Nov. 5, 2001, of a proprietary *Alstroemeria hybrida* selection identified as code number 5782-14, not patented, as the female, or seed, parent with a proprietary *Alstroemeria hybrida* selection identified as code number 97-0-4, not patented, as the male, or pollen, parent. The new *Alstroemeria* was discovered and selected by the Inventor as a flowering plant from within the progeny of the stated cross-pollination in a controlled greenhouse environment in Nieuwveen, The Netherlands on Aug. 27, 2003.

Asexual reproduction of the new *Alstroemeria* by root divisions in a controlled greenhouse environment in Nieuwveen, The Netherlands since Sep. 4, 2003, has shown that the unique features of this new *Alstroemeria* are stable and reproduced true to type in successive generations.

SUMMARY OF THE INVENTION

The new *Alstroemeria* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Konpride'. These characteristics in combination distinguish 'Konpride' as a new and distinct cultivar of *Alstroemeria:*

1. Compact and mounding plant habit.
2. Sturdy and strong plants.
3. Vigorous growth habit.
4. Bright pink-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of the female parent selection.
2. Plants of the new *Alstroemeria* and female parent selection differ in flower color as plants of the female parent selection have purple-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* and the male parent selection differ in flower color as plants of the male parent selection have yellow-colored flowers.

Plants of the new *Alstroemeria* can be compared to plants of the *Alstroemeria hybrida* 'Koserin', disclosed in U.S. Plant Pat. No. 15,996. In side-by-side comparisons conducted in Nieuwveen, The Netherlands, plants of the new *Alstroemeria* differed from plants of 'Koserin' in the following characteristics:

1. Plants of the new *Alstroemeria* were taller but narrower than plants of 'Koserin'.
2. Plants of the new *Alstroemeria* had larger flowers than plants of 'Koserin'.
3. Plants of the new *Alstroemeria* and 'Koserin' differed in flower color as plants of 'Koserin' had yellow and pink-colored flowers.

BRIEF DESCRIPTION OF THE PHOTOGRAPHS

The accompanying colored photographs illustrate the overall appearance of the new *Alstroemeria,* showing the colors as true as it is reasonably possible to obtain in colored reproductions of this type. Colors in the photographs may differ slightly from the color values cited in the detailed botanical description which accurately describe the colors of the new *Alstroemeria*.

The photograph on the first sheet comprises a side perspective view of a typical flowering plant of 'Konpride' grown in a container.

The photograph on the second sheet is a close-up view of a typical flowering stem of 'Konpride'.

DETAILED BOTANICAL DESCRIPTION

The aforementioned photographs and following observations and measurements describe plants of the new *Alstroemeria* grown in Nieuwveen, The Netherlands during the spring and summer in a glass-covered greenhouse in containers. During the production of the plants, day temperatures ranged from 6° C. to 30° C. and night temperatures ranged from 2° C. to 16° C. Plants used for the photographs and description were 26 weeks from planting. Color references are made to The Royal Horticultural Society Colour Chart, 2001 Edition, except where general terms of ordinary dictionary significance are used.

Botanical classification: *Alstroemeria hybrida* 'Konpride'.

Parentage:

*Female, or seed, parent.*—Proprietary *Alstroemeria hybrida* selection identified as code number 5782-14, not patented.

*Male or pollen parent.*—Proprietary *Alstroemeria hybrida* selection identified as code number 97-0-4, not patented.

Propagation:

*Type.*—By root divisions.

*Root description.*—Fibrous, medium in thickness; color, close to 161A.

*Rhizome description.*—Shape: Elongate; rounded. Length: About 5 cm. Diameter: About 8 mm. Texture: Smooth. Color: Close to 161A.

Plant description:

*Plant habit.*—Compact and mounded; freely branching, bushy appearance. Sturdy and strong plants; vigorous growth habit.

*Plant height.*—About 35 cm.

*Plant diameter* (*area of spread*).—About 30 cm.

Stem description:

*Aspect.*—Upright to outwardly spreading.

*Internode length.*—About 1.5 cm to 2.5 cm.

*Strength.*—Strong, sturdy.

*Texture.*—Smooth, glabrous.

*Color.*—Close to 187B; towards the apex, close to 144A.

Foliage description:

*Arrangement.*—Alternate; below the peduncles in a single whorl; sessile.

*Length.*—About 7.2 cm.

*Width.*—About 2.5 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing foliage, upper and lower surfaces: Close to 144A. Fully expanded foliage, upper surface: Close to 141A, venation, close to 153A. Fully expanded foliage, lower surface: Close to 138A; venation, close to N144A.

Flower description:

*Flower type and habit.*—Single cup-shaped flowers arranged in compound umbels. Flowers face upright or outwardly. Perianth segments separate. Freely flowering habit; about four to ten flowers per inflorescence; about 30 to 60 flowers develop per plant.

*Natural flowering season.*—Flowering continuous from the late spring until frost in The Netherlands.

*Fragrance.*—None detected.

*Flower longevity on the plant.*—About one to three weeks; flowers not persistent.

*Flower buds.*—Length: About 4 cm. Diameter: About 1.8 cm. Shape: Ovoid. Color: Close to 155A; towards the apex, close to 64C.

*Umbel height.*—About 10 cm.

*Umbel diameter.*—About 12 cm.

*Flower diameter.*—About 5.6 cm.

*Flower depth* (*height*).—About 6 cm.

*Perianth.*—Arrangement: Six arranged in two whorls, each whorl with two lateral and one median segments. Size, inner perianth: Length, lateral segments: About 5 cm. Width, lateral segments: About 1.9 cm. Length, median segment: About 4.8 cm. Width, median segment: About 2 cm. Size, outer perianth: Length, lateral segments: About 5 cm. Width, lateral segments: About 3.2 cm. Length, median segment: About 4.9 cm. Width, median segment: About 3 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner and outer perianths, lateral and median segments: Attenuate. Margin, inner and outer perianths, lateral and median segments: Entire. Texture, inner and outer perianths, lateral and median segments: Smooth, glabrous. Color, inner perianth: When opening, lateral segments, upper surface: Towards the base, close to 2D; towards the apex, close to 75D; at the apex, close to 143B; stripes, close to 187A. When opening, median segment, upper surface: Towards the base, close to 8D; towards the apex, close to 75B; at the apex, close to 143B; stripes, close to 187A. When opening, lateral segments, lower surface: Towards the base, close to 4C; towards the apex, close to 76C. When opening, median segment, lower surface: Towards the base, close to N155B; towards the apex, close to 75C. Fully opened, lateral segments, upper surface: Towards the base, close to 8C; towards the apex, close to 75B; at the apex, close to 143B; stripes, close to 187A. Color becoming closer to 77C with development. Fully opened, median segment, upper surface: Towards the base, close to N155C; towards the apex, close to 77C; at the apex, close to 143B; stripes, close to 187A. Color becoming closer to 77C with development. Fully opened, lateral segments, lower surface: Close to 2D; towards the base and apex, close to 76B. Fully opened, median segment, lower surface: Close to 75B. Color, outer perianth: When opening, lateral and median segments, upper surface: Close to 75C. When opening, lateral segments, lower surface: Close to 76C. When opening, median segment, lower surface: Close to 75C. Fully opened, lateral and median segments, upper surface: Close to 76B; towards the apex, close to 75A. With development, color becoming closer to 77D. Fully opened, lateral and median segments, lower surface: Close to 76B.

*Pedicels.*—Length: About 4 cm. Diameter: About 3 mm. Strength: Strong. Angle: About 35° C. from vertical. Texture: Smooth, glabrous. Color: Close to 144A.

*Reproductive organs.*—Stamens: Quantity per flower: Six. Anther shape: Oval. Anther size: About 7 mm by 2 mm. Anther color: Close to 191A. Pollen amount: Abundant. Pollen color: Close to 162A. Pistils: Quantity per flower: One. Pistil length: About 4.2 cm. Style length: About 3.1 cm. Style color: Close to 64C. Stigma color: Close to 64B. Ovary color: Close to 144A.

*Fruits.*—Length: About 8 mm. Diameter: About 7 mm. Color: Close to 199A.

Disease/pest resistance: Plants of the new *Alstroemeria* have not been observed to be resistant to pathogens and pests common to *Alstroemeria.*

Garden performance: Plants of the new *Alstroemeria* have been observed to have good garden performance and to tolerate wind, rain and temperatures ranging from about 2° C. to about 30° C.

It is claimed:

1. A new and distinct *Alstroemeria* plant named 'Konpride' as illustrated and described.

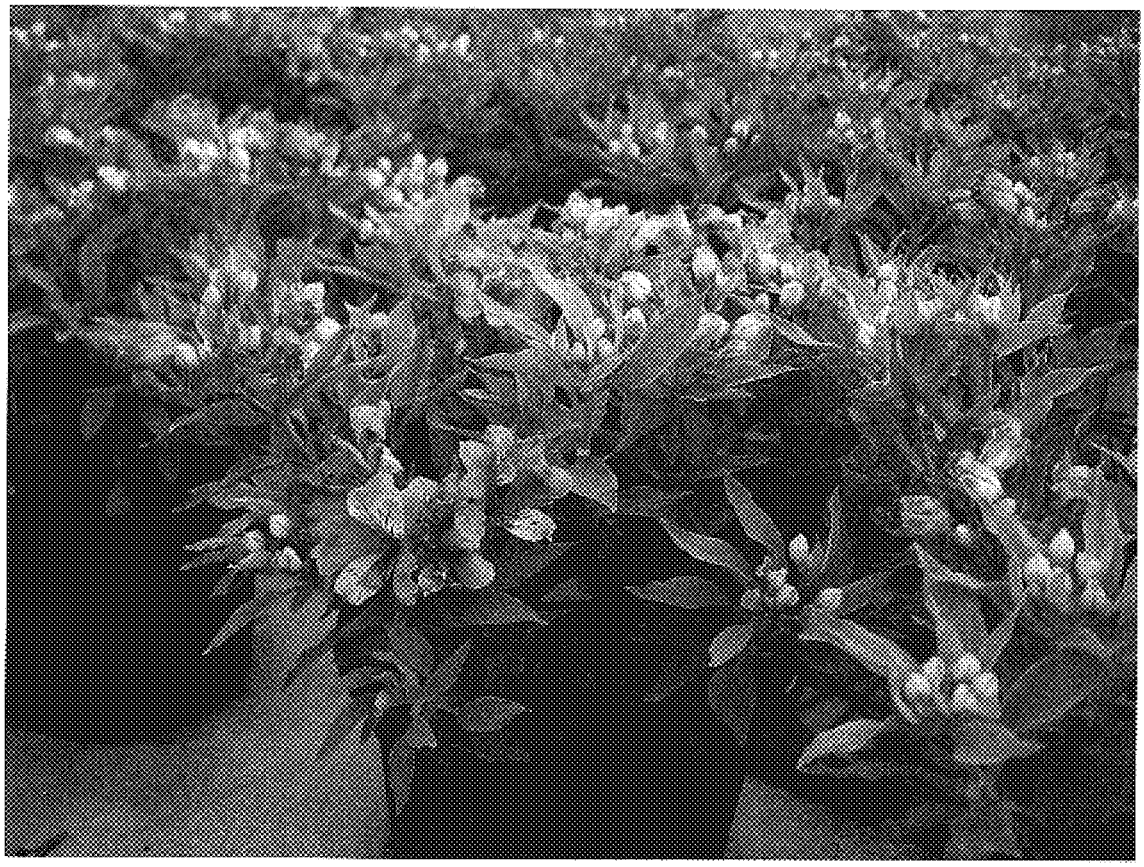

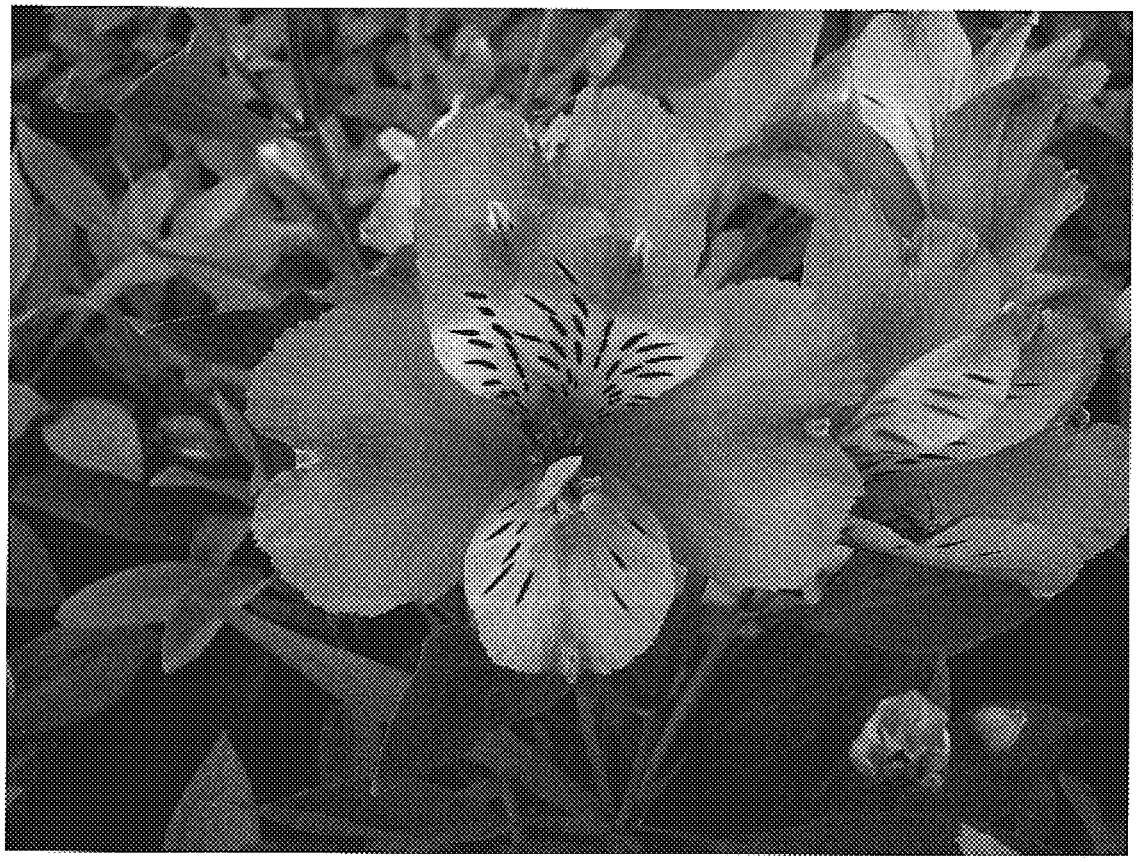

* * * * *